US008441635B2

(12) United States Patent
Schubert et al.

(10) Patent No.: US 8,441,635 B2
(45) Date of Patent: May 14, 2013

(54) MASS SENSOR (75) Inventors: Mathias M. Schubert, Lincoln, NE (US); Eva Schubert, Lincoln, NE (US); Tino Hofmann, Lincoln, NE (US); Daniel Schmidt, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 453 days.

(21) Appl. No.: 12/730,166

(22) Filed: Mar. 23, 2010

(65) Prior Publication Data
US 2010/0245820 A1 Sep. 30, 2010

Related U.S. Application Data (60) Provisional application No. 61/210,899, filed on Mar. 24, 2009.

(51) Int. Cl.
*G01N 15/02* (2006.01)
(52) U.S. Cl.
USPC .......................................... 356/335; 356/336
(58) Field of Classification Search ........... 356/335–344
See application file for complete search history.

(56) References Cited

U.S. PATENT DOCUMENTS

| | | | | | |
|---|---|---|---|---|---|
| 5,554,935 | A | * | 9/1996 | Kraszewski et al. | 324/637 |
| 5,684,276 | A | | 11/1997 | Altemir | 177/210 |
| 6,161,437 | A | * | 12/2000 | Brennan et al. | 73/655 |
| 6,326,563 | B1 | | 12/2001 | Takeuchi et al. | 177/210 |
| 6,389,877 | B1 | * | 5/2002 | Takeuchi et al. | 73/19.03 |
| 6,722,200 | B2 | * | 4/2004 | Roukes et al. | 73/580 |
| 7,304,750 | B2 | * | 12/2007 | Nantel et al. | 356/625 |
| 7,408,147 | B2 | * | 8/2008 | Blick et al. | 250/251 |
| 7,655,269 | B2 | * | 2/2010 | Mayer et al. | 427/2.13 |
| 2007/0207318 | A1 | | 9/2007 | Jin et al. | 428/408 |

FOREIGN PATENT DOCUMENTS

CN 1995488 7/2007

OTHER PUBLICATIONS

Allen et al., "Metallic LiMo$_3$Se$_3$ Nanowire Film Sensors for Electrical Detection of Metal Ions in Water," Langmuir (2008), 24, 7031-7037.
Arbiol et al., "Distributions of Noble Metal Pd and Pt in Mesoporous Silica," Applied Physics Letters (2002), vol. 81, No. 18, 3449-3451.
Espinosa et al., "Nano-scale Testing of Nanowires and Carbon Nanotubes Using a Microelectromechanical System," World Scientific Review vol. 15:32, 1-37 (2007).
Keating et al., "Interdisciplinary Adventures in Bioanalysis," Abstracts, 62nd Southwest Regional Meeting of the American Chemical Society, Houston, TX, United States, Oct. 19-22 (2006), SRM-761.

(Continued)

*Primary Examiner* — Gregory J Toatley
*Assistant Examiner* — Jarreas C Underwood
(74) *Attorney, Agent, or Firm* — Fish & Richardson P.C.

(57) ABSTRACT

A mass sensor is provided for determining the mass of small objects. The mass sensor has a plurality of nanostructures attached to a substrate. The nanostructures and the substrate are irradiated with an electromagnetic wave to determine a first mechanical-electromagnetic resonant frequency of the mass sensor. After a particle is attached to the nanostructures, the substrate and the nanostructures to which the particle is attached are irradiated with an electromagnetic wave to determine a second mechanical-electromagnetic resonant frequency of the mass sensor. A mass of the particle is determined based on a difference between the first and second mechanical-electromagnetic resonant frequencies.

38 Claims, 7 Drawing Sheets

OTHER PUBLICATIONS

Kiuchi et al., "The Piezoresistance Effect of FIB-Deposited Carbon Nanowires Under Severe Strain", J Micromech. Microeng. 18 (2008) 065011 (10pp).

Lee et al., "Enhanced mass sensitivity of stress-free, silicon nanowire-grown microcantilever sensors," Applied Physics Letters 90, pp. 113107-1 to 113107-3, 2007.

McCarthy et al., "Fabrication and Characterisation of Photonic Nanowires," Proceedings of SPIE (2008), vol. 7030 (Nanophotonic Materials V), 703019-1 to 703019-6.

McGary et al., "Magnetic Nanowires for Acoustic Sensors (Invited)," Journal of Applied Physics (2006), 99, 08B310-1 to 08B310-6.

Park et al., "Self-sensing and Interfacial Evaluation of Ni Nanowire/Polymer Composites Using Electro-Micromechanical Technique," Composites Science and Technology, 67:2121-2134, 2007.

Peng et al., "A Microelectromechanical System for Nano-scale Testing of One Dimensional Nanostructures," Sensor Letters (2008), vol. 6, 1-12.

Qi et al., "Molecular Adsorption to $LiMo_3Se_3$ Nanowire Film Chemiresistors," Analytical Chemistry (2006), 78, pp. 1306-1311.

Suzuki et al., "Superconducting NbN Thin-Film Nanowire Detectors for Time-of-Flight Mass Spectrometry," Journal of Low Temperature Physics (2008), 151: 766-770.

Tang et al., "Synthesis of Tetrapodlike Zinc Oxide Nanostructures by Inductive Heating," IEEE Electron Device Letters, vol. 30, No. 12, pp. 1260-1262, Dec. 2009.

Wan et al., "Fabrication and Ethanol Sensing Characteristics of ZnO Nanowire Gas Sensors," Applied Physics Letters, vol. 84, No. 18, pp. 3654-3656, 2004.

Wan et al., "Single-crystalline Sb-doped $SnO_2$ Nanowires: Synthesis and Gas Sensor Application," Chemical Communications (Cambridge, United Kingdom) (2005), (30), 3841-3843.

Zang et al., "Tailoring Zinc Oxide Nanowires for High Performance Amperometric Glucose Sensor," Electroanalysis 19, 2007, No. 9, 1008-1014.

Zheng et al., "Pulse-Loaded Ferroelectric Nanowire as an Alternating Current Source," Nano Letters (2008), vol. 8, No. 10, 3131-3136.

Zhu et al., "A Thermal Actuator for Nanoscale in Situ Microscopy Testing: Design and Characterization," Journal of Micromechanics and Microengineering 16 (2006), 242-253.

Zhu et al., "A Microelectromechanical Load Sensor for in Situ Electron and X-ray Microscopy Tensile testing of Nanostructures," Applied Physics Letters 86, (2005), 013506-1 to 013506-3.

Zhu et al., "An Electromechanical Material Testing System for in Situ Electron Microscopy and Applications," Proceedings of the National Academy of Sciences of the United States of America (2005), vol. 102, No. 41, 14503-14508.

\* cited by examiner

FIG. 6

MASS SENSOR

CROSS-REFERENCE TO RELATED APPLICATIONS

This application is claims priority to U.S. Provisional Application Ser. No. 61/210,899, having an official filing date of Mar. 24, 2009. The above application is incorporated herein by reference in its entirety.

STATEMENT AS TO FEDERALLY SPONSORED RESEARCH

This invention was made with government support under Grant No. NSF-ECCS-0824920 and NSF-ECCS-0846329 awarded by NSF. The government has certain rights in the invention.

TECHNICAL FIELD

This subject matter is generally related to mass sensors.

BACKGROUND

It is useful to be able to determine the mass of small particles or molecules. For example, by measuring the mass of a bio-molecule, one may be able to determine the type of the bio-molecule being tested. Mass sensors that are sensitive to small quantities of materials are useful in, for example, gas chromatography or mass spectrometry. There are many types of mass sensors that can determine the mass of small particles. For example, one type of mass sensor is the quartz crystal microbalance sensor, which uses a thin crystalline quartz disc placed between two electrodes. Another type of mass sensor is the microcantilever-based sensor that has several silicon nanowire-grown cantilevers. Yet another type of mass sensor is the surface acoustic wave sensor, which uses perturbations in surface acoustic waves to determine mass.

SUMMARY

In general, in one aspect, a method of determining a mass of a particle is provided. The method includes providing a mass sensor having a plurality of nanostructures on a substrate, irradiating the nanostructures and the substrate with an electromagnetic wave to determine a first mechanical-electromagnetic resonant frequency of the mass sensor, attaching a particle to the nanostructures, irradiating the substrate and the nanostructures to which the particle is attached with an electromagnetic wave to determine a second mechanical-electromagnetic resonant frequency of the mass sensor, and determining a mass of the particle based on a difference between the first and second mechanical-electromagnetic resonant frequencies.

Implementations may include one or more of the following features. The nanostructures can include nanocoil structures. The nanostructures can include chiral nanostructures. The nanostructures can include metal nanostructures, and the substrate can include a semiconductor substrate. The electromagnetic wave can have a frequency that matches the mechanical-electromagnetic resonant frequency of the nanostructures. The nanostructures can have a mechanical eigenresonance that measurably influence an electromagnetic eigenresonance of the mass sensor, the influence of the mechanical eigenresonance on the electromagnetic eigenresonance being measurable based on measurements of properties of the electromagnetic wave that is transmitted through or reflected from the mass sensor. Determining the mass can include comparing the difference between the first and second mechanical-electromagnetic resonant frequencies with information representing a mapping between changes in mechanical-electromagnetic resonant frequencies and mass. The method can include detecting electromagnetic waves that are reflected from or transmitted through the nano structures, and determining the first and second mechanical-electromagnetic resonant frequencies based on the detected electromagnetic waves. Attaching a particle can include selectively capturing a particle that belongs to a type of particles that match a shape of the nanostructures.

In general, in another aspect, an apparatus including a mass sensor is provided. The mass sensor includes a substrate and a plurality of nanostructures attached to the substrate. The nanostructures have a mechanical resonant frequency that varies depending on a mass of an object coupled to the nanostructures, the nanostructures and the substrate having a mechanical-electromagnetic resonant frequency such that a resonance occurs when the nanostructures and the substrate are irradiated by an electromagnetic wave having a frequency substantially equal to the mechanical-electromagnetic resonant frequency. The nanostructures and the substrate are configured such that changes in the mechanical-electromagnetic resonant frequencies correspond to the mass of the object according to a predetermined mapping between changes in mechanical-electromagnetic resonant frequencies and mass.

Implementations may include one or more of the following features. The nanostructures can include nanocoil structures. The nanostructures can be configures such that at least 10% of the nanostructures each includes a nanowire having a diameter less than 500 nm. The nanostructures can include chiral nanostructures. The nanostructures and the substrate can have dimensions and materials configured such that the mechanical-electromagnetic resonant frequency of the mass sensor is in a range from 0.1 to 20.5 terahertz, the mechanical-electromagnetic resonant frequency being adjustable depending on a bias voltage applied to the substrate. The nanostructures can be made of metal, and the substrate can be made of a semiconductor. The plurality of nanostructures can include a first group of nanostructures and a second group of nanostructures, the first group of nanostructures having a first lateral spacing period, the second group of nanostructures having a second lateral spacing period that is different from the first lateral spacing period. The apparatus can include a first electrode and a second electrode to receive a bias voltage, the first and second electrodes being coupled to the substrate to provide the bias voltage to the substrate. The nanostructures can have shapes configured to selectively capture a predetermined type of objects. The nanostructures can be treated to have functional attachments that are configured to selectively capture a predetermined type of objects. The functional attachments can include peptides.

In general, in another aspect, a system for measuring a mass of an object is provided. The system includes a mass sensor, an analyzer, and a data processor. The mass sensor includes a substrate and a plurality of nanostructures attached to the substrate. The analyzer determines a mechanical-electromagnetic resonant frequency of the mass sensor. The data processor determines a mass of an object attached to the nano structures based on a difference between a first mechanical-electromagnetic resonant frequency of the mass sensor measured before the object is attached to the nano structures and a second mechanical-electromagnetic resonant frequency of the mass sensor measured after the object is attached to the nano structures.

Implementations may include one or more of the following features. The nanostructures can include nanocoil structures. The nanostructures can include chiral nanostructures. The nanostructures can include metal, and the substrate can include a semiconductor. The analyzer can include an ellipsometer. The system can include a voltage source to provide a bias voltage to the substrate, and a controller to control the voltage source to adjust the bias voltage to change the mechanical-electromagnetic resonant frequency of the mass sensor. The nanostructures and the substrate can have dimensions and materials configured such that a mechanical eigenresonance of the nanostructures couples with an electromagnetic eigenresonance of the mass sensor, and the coupled mechanical-electromagnetic resonant frequency matches a frequency range of the analyzer, which uses electromagnetic waves to determine the mechanical-electromagnetic eigenresonance of the mass sensor. The system can include a storage to store information representing a mapping between changes in the mechanical-electromagnetic resonant frequency and mass. The nanostructures can have shapes configured to selectively capture a predetermined type of objects. The nanostructures can be treated to have functional attachments that are configured to selectively capture a predetermined type of objects. The plurality of nanostructures can include a first group of nanostructures and a second group of nanostructures, the first group of nanostructures having a first lateral spacing period, the second group of nanostructures having a second lateral spacing period that is different from the first lateral spacing period. The mass of the object can be determined based on a first difference in mechanical-electromagnetic resonant frequencies in a first region of the mass sensor having the first group of nanostructures and a second difference in mechanical-electromagnetic resonant frequencies in a second region of the mass sensor having the second group of nanostructures.

These features allow a user to measure the mass of small molecules in a cost efficient manner.

DETAILED DESCRIPTION

This disclosure relates to a mass sensor having nanostructures deposited on a substrate. The sensor has a mechanical-electromagnetic resonant frequency that changes in response to attachment of an object. The mass of the object can be determined based on the amount of change in the resonant frequency. The resonant frequency can range from, for example, 0.1 to 20 terahertz, and the sensor can be sensitive to small particles, for example, bio-molecules, drug molecules, short DNA sequences, and short RNA sequences.

Figure 1:
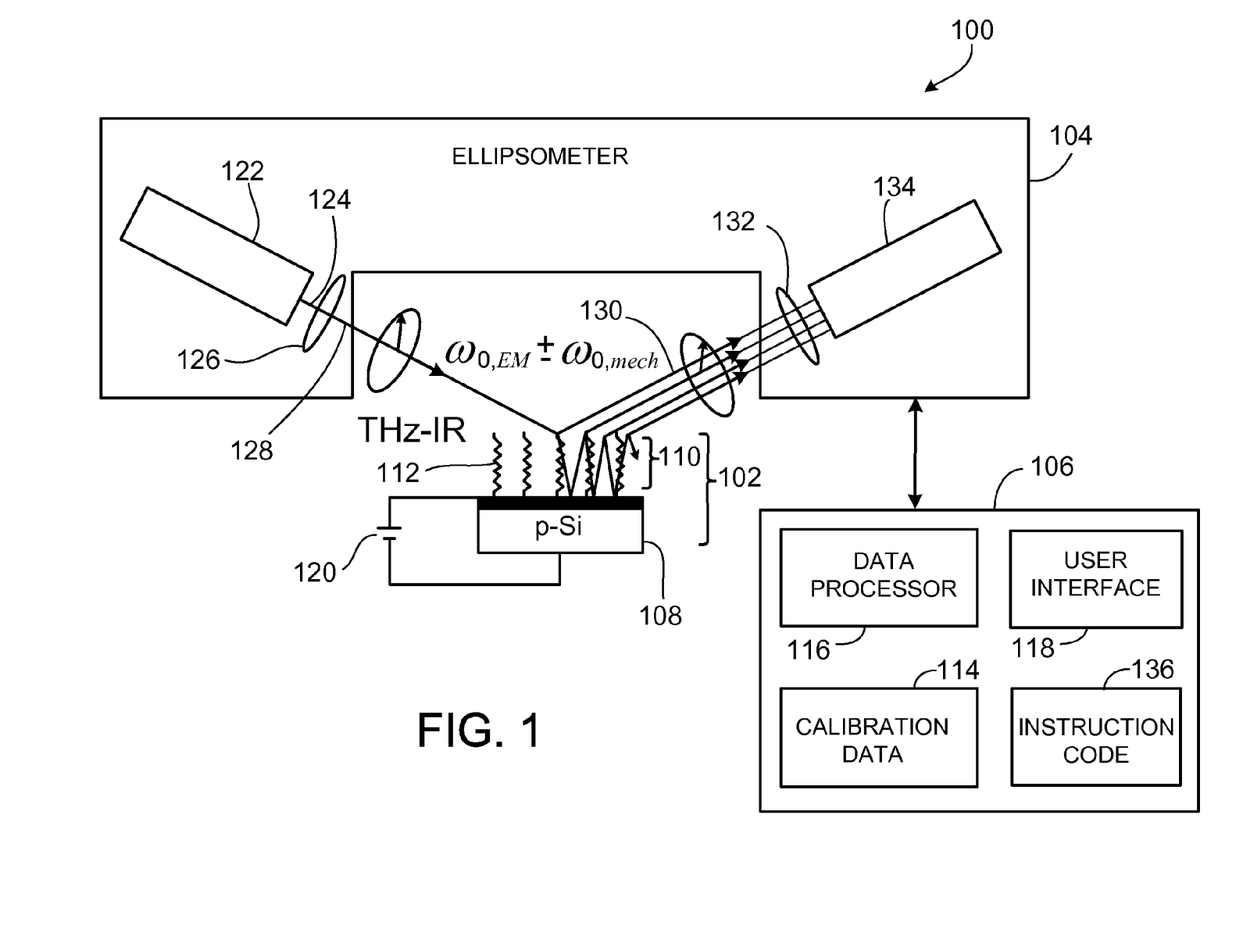
FIG. 1 is a diagram of an example mass sensing system.

Referring to FIG. 1, in some implementations, a mass sensing system 100 for determining a mass of a small object includes a mass sensor 102, an ellipsometer 104, and a data processing module 106. The mass sensor 102 includes a substrate 108 on which a sculptured thin film 110 is formed. The sculptured thin film 110 includes nanostructures 112 that can be, for example, columns, spirals, screws, or zig-zag structures. The nanostructures 112 can be chiral (such as nanocoils) or achiral (such as posts). A power source 120 provides a bias voltage to the substrate 108.

The nanostructures have elasticity and can deform when a force is applied to the nanostructures. For example, the nanostructures may be compressed and uncompressed, similar to a spring, or bent and unbent, similar to a flexible rod. The nanostructures may have mechanical (vibrational) resonances at particular frequencies, referred to as the mechanical resonant frequencies or mechanical eigenfrequencies.

The mechanical resonant frequency of a nanocoil can be approximated using the formula below, which are similar to formulas used to determine the resonant frequencies of a spring:

$$\omega_{0,mech} = \sqrt{\frac{D}{3m}} \quad D = \frac{Gr^4}{4R^3n}. \quad \text{(Equation 1)}$$

In Equation 1 above, $\omega_{0,mech}$ is the mechanical resonant frequency, m is the mass of the nanocoil, G is the torsion module constant, r is the inner radius, R is the outer radius, and n is the number of turns. In some examples, the mechanical resonance frequencies can range from 0.1 THz to 0.5 THz.

The mass sensor 102 may exhibit resonance when irradiated with electromagnetic waves having a particular frequency. Without being limited by any theory presented herein, the sculptured thin film 110 and the substrate 108 may be modeled as an inductor-capacitor (LC) resonant circuit that reacts to electromagnetic waves. The frequencies at which the mass sensor 102 exhibits resonance when irradiated with electromagnetic waves are referred to as the electromagnetic resonant frequencies or electromagnetic eigenfrequencies of the mass sensor 102. In some examples, the sculptured thin film 110 and the substrate 108 are configured such that the resonance occurs in the infrared range, which is within the range of light beams that can be generated and measured by the ellipsometer 104.

The electromagnetic resonant frequency of the mass sensor 102 that uses nanocoils can be approximated using the formulas below:

$$\omega_{0,EM} = \sqrt{\frac{1}{LC}}, \quad L = \frac{\mu_0 n^2 A_i}{l}, \quad C(U) = \frac{\varepsilon_0 \varepsilon A_c}{d_c(U)} \quad \text{(Equation 2)}$$

where $\omega_{0,EM}$ is the electromagnetic resonant frequency, L is the coil inductivity, C is the depletion layer capacitance, n is the number of turns in the nanocoil, $\mu_0$ and $\varepsilon_0$ are the vacuum permittivity and permeability, l is the length of the coil, $A_c$ is the nanowire cross section area of the coil, $A_i$ is the footprint (cross section area) of the coil, ∈ is the host material dielectric constant, and $d_c(U)$ is the depletion layer width. The depletion layer width $d_c(U)$ may be changed by adjusting the diode bias voltage provided by the power source 120. In some examples, the electromagnetic resonant frequencies can range from 0.1 THz to 20 THz.

Similar to photon-phonon coupling in bulk materials, the mechanical resonance and the electromagnetic resonance of the mass sensor 102 may be coupled such that the mass sensor 102 shows mechanical-electromagnetic resonance frequencies at $\omega_{0,EM} \pm \omega_{0,mech}$, which may occur in the range between, for example, 0.5 THz to 20.5 THz. The mechanical-electromagnetic resonant frequencies can be measured by the ellipsometer 104. The ranges of the mechanical resonant frequencies, the electromagnetic resonant frequencies, and the coupled mechanical-electromagnetic resonant frequencies are not limited to those described above and can vary depending on the configurations of the nanostructures and substrate (for example, the dimensions and shapes of the nanostructures), and the bias voltage applied to the substrate.

The ellipsometer 104 includes a light source 122 that generates a light beam 124, which passes a first polarizer 126 to form a polarized light beam 128. The light beam 128 is directed towards the surface of the mass sensor 102, and the light beam 130 reflected from the mass sensor 102 passes a second polarizer 132 before reaching a detector 134. The detected light beam is analyzed to determine the optical properties (such as the resonant frequency) of the mass sensor 102.

When an object is attached to the nanostructure 112, both the mechanical and electromagnetic resonance frequencies may change (in most cases, be reduced), but the change in mechanical resonance frequency is much larger than the change in electromagnetic resonance frequency. The amount of reduction in the resonant frequency may be indicative of the mass of the object.

The nanostructures are configured to have a mechanical eigenresonance that measurably influence an electromagnetic eigenresonance of the mass sensor. The influence of the mechanical eigenresonance on the electromagnetic eigenresonance can be measured based on complex measurements (e.g., measurements of amplitude and phase) of electromagnetic waves transmitted through or reflected from the mass sensor. The electromagnetic waves can have normal or oblique incidence.

In general, as the size of the nanostructure 112 increases, the mechanical resonant frequency decreases, and the electromagnetic resonant frequency increases. The coupling of the mechanical eigenresonance and the electromagnetic eigenresonance occurs when the two eigenresonances are within, for example, two or three orders of magnitude. In designing the nanostructures 112, one can start with Equations 1 and 2 and select parameters for the nanostructures 112 such that $\omega_{0,mech}$ is within two or three orders of magnitude of $\omega_{0,EM}$. The parameters can be adjusted such that there is a measurable difference in the coupled mechanical-electromagnetic resonant frequencies before and after attachment of an object to be measured.

The design of the nanostructures may depend on the sensitivity required for the mass sensor. For example, a mass sensor that is used to detect an object having a smaller mass may be configured differently compared to a mass sensor that is used to detect an object having a larger mass.

In some examples, the system 100 is calibrated by analyzing objects with known mass and measuring the changes in resonant frequency of the mass sensor 102 before and after the objects with known mass are attached to the mass sensors 102. A table having information that maps changes in the mechanical-electromagnetic resonant frequency to mass is established and stored as calibration data 114.

When a new object is analyzed, the mechanical-electromagnetic resonant frequencies of the mass sensor 102 before and after attachment of the object is measured by the ellipsometer 104, and a data processor 116 determines the change in the mechanical-electromagnetic resonant frequency. The data processor 116 compares the change in mechanical-electromagnetic resonant frequency with the calibration data 114 to determine the mass of the object.

A user interface 118 is provided for interacting with a user, including receiving commands and outputting the mass of the measured object. The data processing module 106 may include a storage 136 to store instruction code that is executed by the data processor 116 to perform the various tasks described here.

An advantage of the mass sensor 102 is that it can measure minute mass quantities. For example, the mass sensor 102 can be used as a biosensor for sensing various types of biomolecules. Another advantage is that the mass sensor 102 allows small amounts of materials to be probed using light, and can be used with ellipsometers of many different makes and models.

In some implementations, the nanostructures 112 can be generated in a self-organized growth process by using glancing angle deposition (GLAD) accompanied with a controlled substrate motion. For example, the substrate 108 can be rotated continuously to form nanocoils. Sculptured thin films with tailored designs can be grown from a broad variety of different materials (semiconductors, insulators, dielectrics, and metals) by using physical vapor deposition methods. Glancing angle deposition is a method to generate three-dimensional (3D) chiral nanostructures from a concurrent growth mechanism due to geometrical shadowing in combination with kinetic limitation for surface adatoms. This technique uses a particle flux reaching the substrate under an oblique angle of incidence (for example, greater than 80°). These conditions support a columnar growth, and the instantaneous change of the growth direction due to a simple variation of the incident vapor flux (by substrate rotation) allows for the fabrication of 3D nanostructures with manifold morphologies.

Some description of the principles of sculptured thin film preparation by glancing angle deposition can be found in "Uniaxial magnetic anisotropy in cobalt films induced by oblique deposition of an ultrathin cobalt underlayer," by M. T. Umlor, Appl. Phys. Lett. 87, 082505 (2005).

Glancing angle deposition sculptured thin film can be prepared using, for example, semiconducting or insulating materials, such as silicon, silicon dioxide, $TiO_2$. Metal (for example, Co, Cu, W, Al) nanorods, whiskers, and nanopillars can also be grown using glancing angle deposition. Sculptured thin films from metal with morphologies that render chiral structures can also be grown using glancing angle deposition. Metal nanostructure sculptured thin films with chiral geometries may have optical effects due to the coupling between magnetic and electric fields. Electric field-driven charge currents along, for example, the cork screw path of a screw-like nanostructure may produce local magnetic field effects and vice versa.

In some implementations, the growth conditions can be chosen such that geometries and dimensions of screw-like building blocks are suitable for the electromagnetic eigenresonances within the terahertz and infrared spectral range. In some implementations, the sculptured thin film can include an array of sub-wavelength metallic thin film double-ring resonators, and the substrate can be a doped semiconductor substrate. The substrate-film structure reveals diode characteristics for transverse electric currents. The junction region within the substrate acts as a capacitance that can be tuned by an appropriate bias potential.

In some implementations, the nanostructures 112 are chiral aluminum nanowires, and the substrate 108 is a p-type silicon substrate. The mass sensor 102 has resonance at infrared wavelengths. The aluminum nanowires are grown on the silicon substrate using glancing angle deposition, and the nanostructure shape can be varied by, for example, applying a clockwise substrate rotation yielding to chiral aluminum nanoscrews. The screw-like sculptured thin film, when analyzed using infrared spectroscopic ellipsometry (IRSE), may show equidistant resonance features. For example, the mass sensor 102 may show a series of equidistant resonances separated by the energy equivalent of about 7.5 terahertz.

In some implementations, the mass sensor 102 can include two or more substrates 108, in which the same nanostructures 112 are attached to the substrates 108, but the lateral spacing periods of the nanostructures are different for different substrates 108. Particles having the same mass but different sizes may affect the resonant frequency differently. For example, smaller denser particles may strongly affect fewer nanostructures, causing a larger shift in resonant frequency from the nanostructures affected and no shift in resonance from the unaffected nanostructures. By comparison, larger and less dense particles may affect more nanostructures, causing a smaller shift in resonant frequency in a larger number of affected nanostructures.

In some examples, the two or more substrates having various lateral spacing of the same nanostructures are used to detect objects of the same type (e.g., each of the substrates captures the same DNA or RNA segment), and the measurements of changes in resonant frequencies are performed on the two or more substrates. The measurements on different substrates can be performed sequentially or in parallel (e.g., using multiple probe beams). For larger molecules, each molecule may contact a larger number of nanostructures, there is a larger difference in the number of nanostructures affected by the molecule among different substrates, so one may detect different resonant frequency shifts among the different substrates. For smaller molecules, because each molecule contacts a smaller number of nanostructures, the difference in the resonant frequency shifts among the different substrates may be smaller or insignificant.

A calibration of the system 100 may be performed such that the resonant frequency shifts are measured for different molecules having the same (or similar) mass but different densities (and thus different sizes). The calibration data 114 may include information about resonant frequency shifts for various mass, and for various sizes that correspond to a given mass. When measurements of a molecule (or other objects) with an unknown mass are compared to the calibration data 114, interpolation and extrapolation may be performed if there is no exact match between the measurement data and the calibration data 114.

Instead of using a mass sensor having several substrates, it is possible to use a single substrate having various regions in which different regions have nanostructures with different lateral spacing periods. It is also possible to use a set of mass sensors, each mass sensor having one substrate, and different mass sensors in the set have nanostructures with different lateral spacing periods.

Figure 2A:
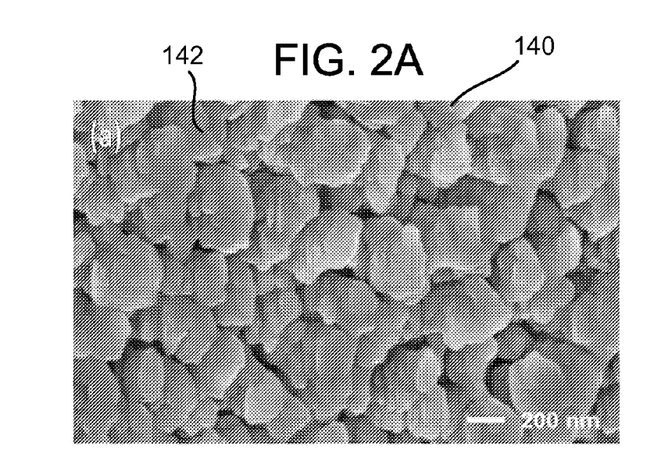
FIGS. 2A and 2B are surface and cross-section scanning electron microscopy (SEM) images, respectively, of an aluminum plate-like sculptured thin film deposited on [100] p-type silicon.
Figure 2B:
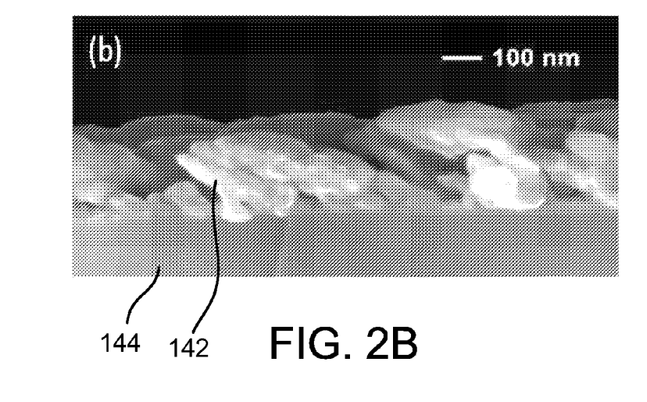
Figure 2C:
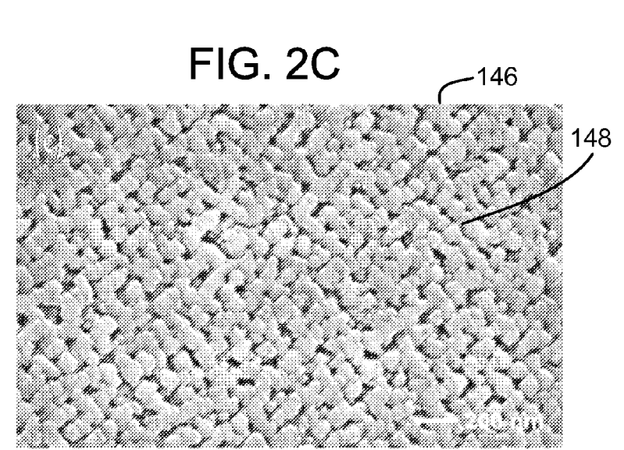
FIGS. 2C and 2D are surface and cross-section scanning electron microscopy images, respectively, of an aluminum screw-like sculptured thin film deposited on [100] p-type silicon.
Figure 2D:
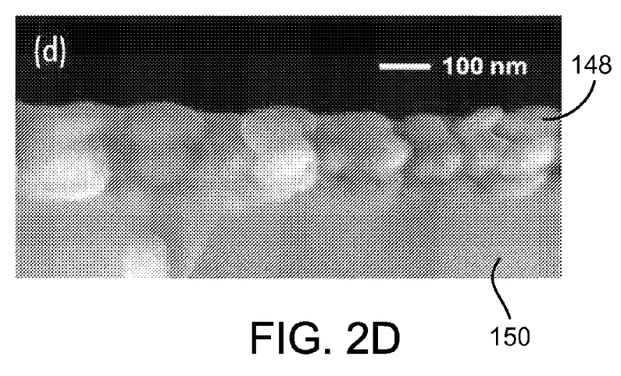

FIGS. 2A to 2D are scanning electron microscopy images of aluminum sculptured thin films deposited on [100] p-type silicon. FIG. 2A is a surface scanning electron microscopy image 140 of an aluminum plate-like sculptured thin film 142 deposited on [100] p-type Si. FIG. 2B is a cross-section scanning electron microscopy image 144 of an aluminum plate-like sculptured thin film 142 deposited on [100] p-type silicon. FIG. 2C is a surface scanning electron microscopy image 146 of an aluminum screw-like sculptured thin film 148 deposited on [100] p-type silicon. FIG. 2D is a cross-section scanning electron microscopy image 150 of an aluminum screw-like sculptured thin film 148 deposited on [100] p-type silicon.

The optical responses of both samples were measured by infrared spectroscopic ellipsometry in the spectral region from a frequency ω of about 130 cm$^{-1}$ to about 2500 cm$^{-1}$ (ν=5 THz to ν=75 THz). Spectroscopic ellipsometry can be used to determine the dielectric functions and thickness of films within layered samples. Spectroscopic ellipsometry measures the change of polarization upon reflection (or transmission), which can be described by the complex reflectance ratio ρ by $\rho = r_p/r_s = \tan \Psi \exp i\Delta$, in which $r_p$ and $r_s$ are the reflection coefficients for light polarized parallel (p) and perpendicular (s) to the plane of incidence, respectively, and $\Psi$ and $\Delta$ are the ellipsometry parameters. Spectroscopic ellipsometry spectra are analyzed by a model lineshape analysis that takes into account of the layered structures of a given sample. Physical model lineshape functions can be implemented to best-match the frequency dependence of the underlying dielectric function of the materials involved. Here, for simplicity of analyses, the optical response is assumed to be caused by a homogeneous film of thickness d.

Figure 3A:
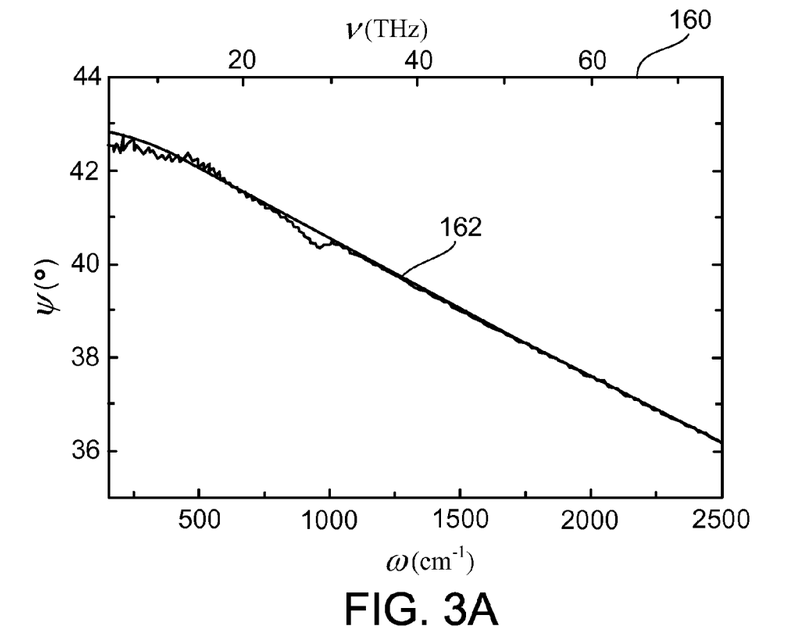
FIG. 3A shows the optical response of the plate-like sculptured thin film of FIGS. 2A and 2B.

FIG. 3A is a graph 160 showing an optical response 162 of the plate-like sculptured thin film 142 of FIGS. 2A and 2B, as measured by infrared spectroscopic ellipsometry.

Figure 3B:
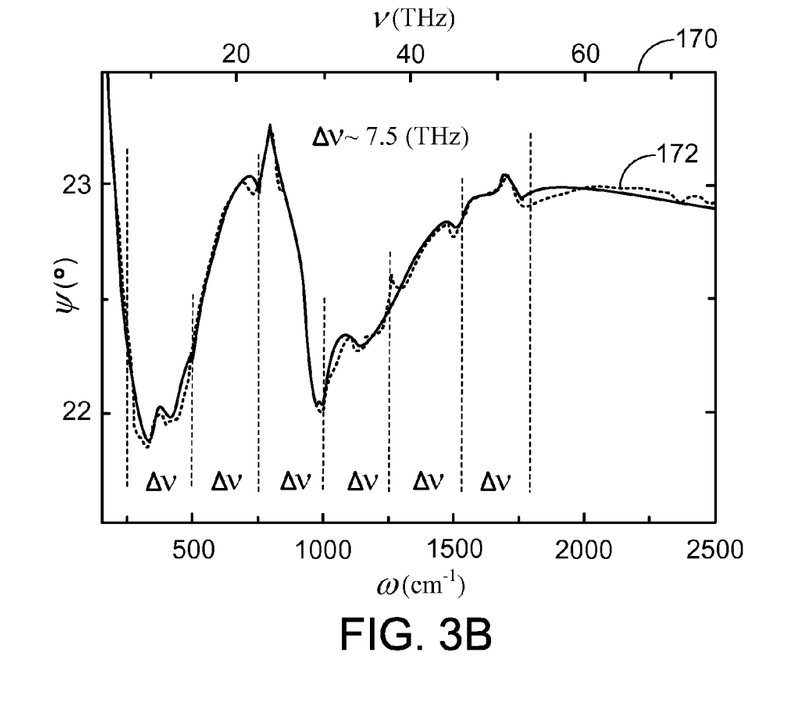
FIG. 3B shows the optical responses of the screw-like sculptured thin film of FIGS. 2C and 2D.

FIG. 3B is a graph 170 showing an optical response 172 of the screw-like sculptured thin film 148 of FIGS. 2C and 2D, also measured by infrared spectroscopic ellipsometry. In the figures, only the $\Psi$ spectra are shown.

As can be seen in FIG. 3A, the plate-like sculptured thin film 142 resembles the behavior of a homogeneous optically opaque metal film, where absorption due to free electrons causes a rather flat slope. The so-called two-phase (substrate-ambient) model is sufficient to calculate the infrared spectroscopic ellipsometry data, where the dielectric function of the metal sculptured thin film is parameterized using the classical Drude model. The best-match specific resistivity of $\rho_{plate} = 10.9 \times 10^{-5}$ Ωcm, and a mean free scattering time of $\tau_{plate} = 1.0$ fs describes the infrared optical behavior of the plate-like film well (see solid line in FIG. 3A). No further model parameters are required. The Drude parameters obtained for this plate-like aluminum sculptured thin film indicate a lower conductivity and shorter electron average mean free scattering time due to the nanoporosity of the sculptured thin film sample than for bulk aluminum ($\rho_{bulk} = 0.29 \times 10^{-5}$ Ωcm, and $\tau_{bulk} = 6.7$ fs).

As shown in FIG. 3B, the screw-like sculptured thin film 148 infrared spectroscopic ellipsometry sample response is different from the plate-like sample 142. The infrared spectroscopic ellipsometry data shown in FIG. 3B are comparable to a dielectric thin film with spectrally varying absorption features, such as lattice modes in amorphous or polycrystalline semiconductors deposited on a silicon substrate. There are apparently equidistant resonance features with a spectral separation $\Delta \nu$ equal to about 7.5 THz, which are indicated by the vertical dashed lines in FIG. 3B. The solid line in FIG. 3B represents the best-match calculated infrared spectroscopic ellipsometry data using three-phase (substrate-film-ambient) model approach. The optical properties (dielectric function) for the screw-like sculptured thin film sample were modeled using sums of Lorentzian oscillators with resonance frequencies to account for each of the resonance feature seen in FIG. 3B.

Without being bound by any theory presented herein, the equally separated resonance series for the screw-like sculptured thin film may originate from coupled (overtone) inductance-capacitance (LC) resonances within the aluminum nanoscrew network, where each turn of the coils acts as an inductance (L component). The p-type silicon substrate forms a Schottky-barrier capacitor, and each nanocoil is connected to a capacitor area (C component). The appearance of overtones may be due to non-linear coupling effects, or due to laterally contacted individual coils.

Occurrence of higher order harmonics of resonant charging and discharging of the Schottky diode depletion region may also be a possible explanation for the occurrence of equally separated resonance series. The LC resonance circuit frequency $\omega_{0,EM}$ is inversely proportional to the coil inductivity L and the depletion layer capacitance C, as described in Equation 2 above.

Table 1 below shows calculated loss-free electromagnetic resonance circuit frequencies ν for a chiral (hollow metal coil) sculptured thin film resonator structure with different dimensions. The coil is attached to the surface of a p-type silicon substrate to form a Schottky diode with a depletion layer $d_c$.

TABLE 1

| $A_c$ (cm$^2$) | l (μm) | n | $d_c$ (nm) | L (Vs/A) | C (As/V) | ν (THz) |
|---|---|---|---|---|---|---|
| 4 × 10$^{-10}$ | 2.5 | 10 | 100 | 8 × 10$^{-12}$ | 3.5 × 10$^{-18}$ | 29 |
|  |  |  | 10 |  | 3.5 × 10$^{-17}$ | 9 |
|  |  |  | 5 |  | 7.0 × 10$^{-17}$ | 6.7 |
|  | 1.25 | 5 | 10 | 1 × 10$^{-12}$ | 3.5 × 10$^{-17}$ | 27 |
|  |  |  | 5 | 1 × 10$^{-12}$ | 7.0 × 10$^{-17}$ | 19 |

The shapes of the nanostructures 112 can be configured to selectively capture certain types of compounds or molecules, such as certain nucleotides, proteins, or drug molecules. This allows the mass sensor 102 to monitor the existence of certain compounds or molecules. For example, the mass sensor 102 can be used to detect certain toxins.

Figure 4A:
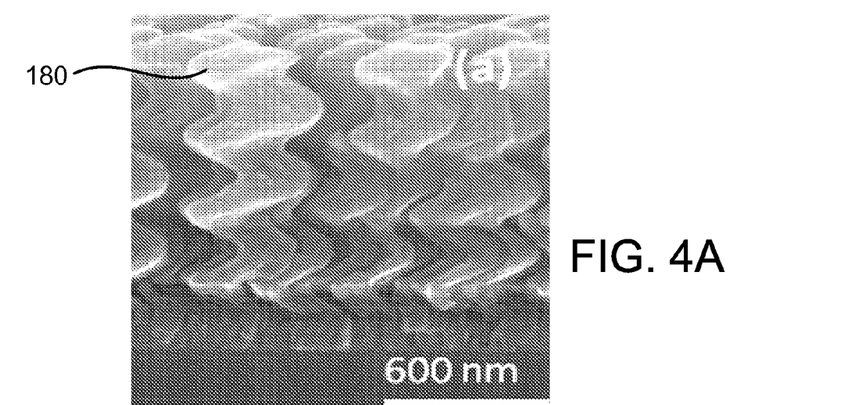
FIG. 4A is a side view scanning electron microscopy of chiral nanostructures that have hollow cores.

Referring to FIG. 4A, in some examples, the mass sensor 102 can include chiral nanostructures have hollow cores 180. For example, the inner diameter of the chiral nanostructure can range from 2 to 200 nm, the length of the chiral nanostructure can range from 5 to 5000 nm, and the spatial separation period can range from 5 to 1000 nm. The attachment of the object to be measured can occur within nanostructures (i.e., in the hollow cores).

Examples of objects that can be attached to the chiral nanostructures having hollow cores include the following:
  Single and double-helix, single-nucleotide unit up to 15,000-nucleotide unit long unfolded deoxyribonucleic acid (DNA) polymers;
  Ribonucleic acid (RNA);
  Short (about 22 nucleotide) RNA sequences (microRNA);
  Few-hundreds nucleobases single-stranded RNA (viroids);
  Left- or right-handed stereoisomeric molecules (entantiomers; control for stereoisomeric composition of drug molecules=pharmacokinetic evaluation) of sizes up to 5000 nm length and 1000 nm diameter; and
  Helical protein shells of viruses (helical capsids).

Figure 4B:
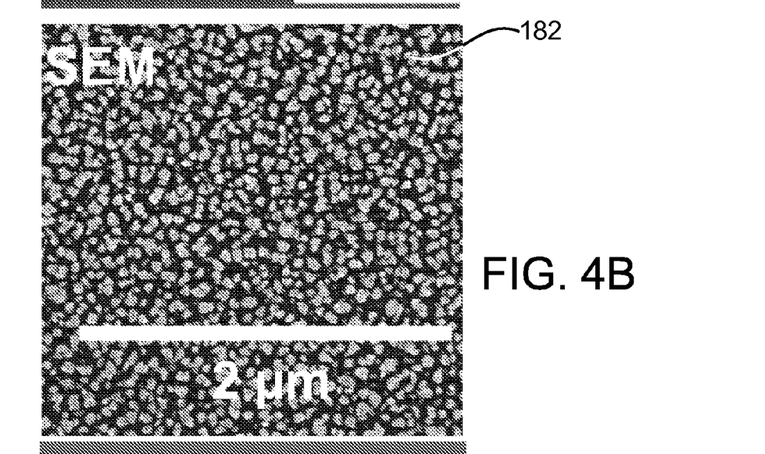
FIG. 4B is a top view scanning electron microscopy image of chiral nanostructures that have closed cores.

Referring to FIG. 4B, in some examples, the mass sensor 102 can include chiral nanostructures have solid cores 182. For example, the outer diameter of the chiral nanostructures have solid cores 182 can range from 5 to 500 nm, the length of the chiral nanostructures can range from 50 to 5000 nm, and the spatial separation period can range from 5 to 1000 nm. The attachment of the objects to be measured can occur between nanostructures.

Examples of objects that can be attached to the chiral nanostructures having solid cores include the following:
  Single and double-helix, single-nucleotide unit up to 15,000-nucleotide unit long unfolded deoxyribonucleic acid (DNA) polymers;
  Ribonucleic acid (RNA);
  Short (about 22 nucleotide) RNA sequences (microRNA);
  Left- or right-handed stereoisomeric molecules (pharmacokinetic evaluation) for sizes larger than 5000 nm length and 1000 nm diameter; and
  Helical protein shells of viruses (helical capsids).

Figure 4C:
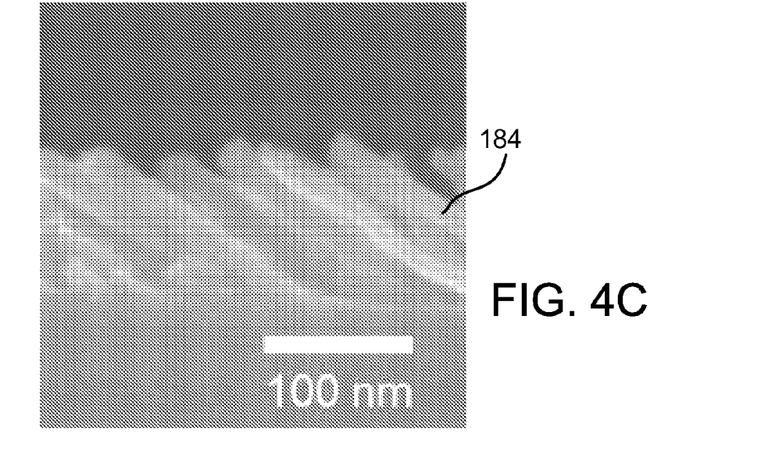
FIG. 4C is a side view scanning electron microscopy image of achiral nanostructures, including slanted posts.
Figure 4D:
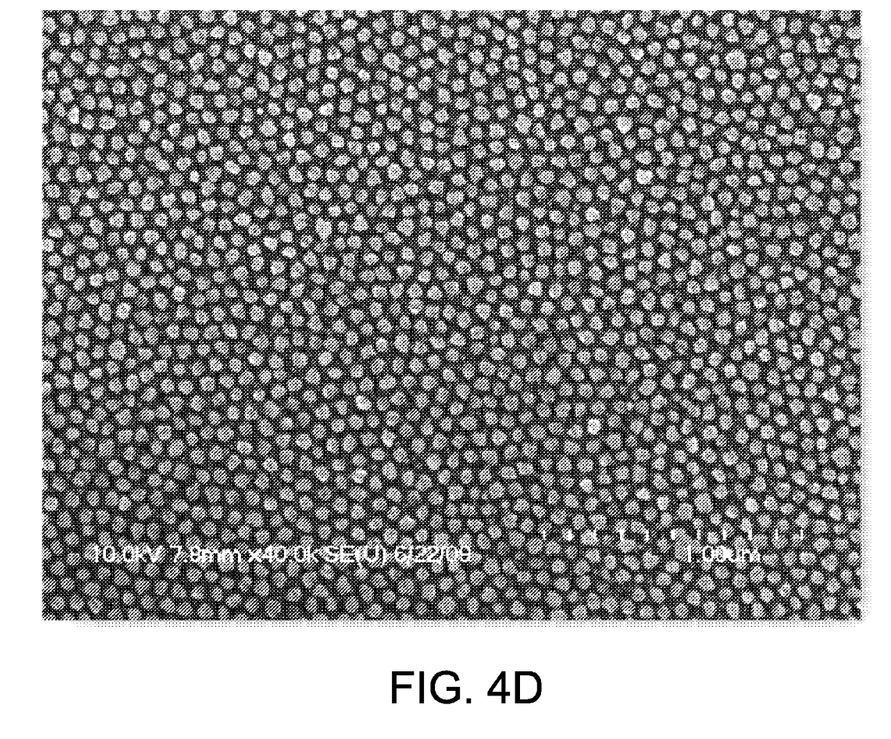
FIG. 4D is a top view scanning electron microscopy image of vertical posts.

Referring to FIG. 4C, in some examples, the mass sensor 102 can include achiral nanostructures, such as vertical posts and slanted posts 184. For example, the outer diameter of the achiral nanostructures can range from 5 to 500 nm, the length of the nanostructures can range from 50 to 5000 nm, and the spatial separation period can range from 5 to 1000 nm. The attachment of the objects to be measured can occur between the nanostructures. FIG. 4D is a top view scanning electron microscopy image of vertical posts.

Examples of objects that can be attached to the achiral nanostructures include the following:
  Viroids;
  Icosahedral protein shells of viruses (icosahedral capsids);
  Viruses; and
  Unicellular, prokaryote, microorganisms (bacteria).

Figure 5:
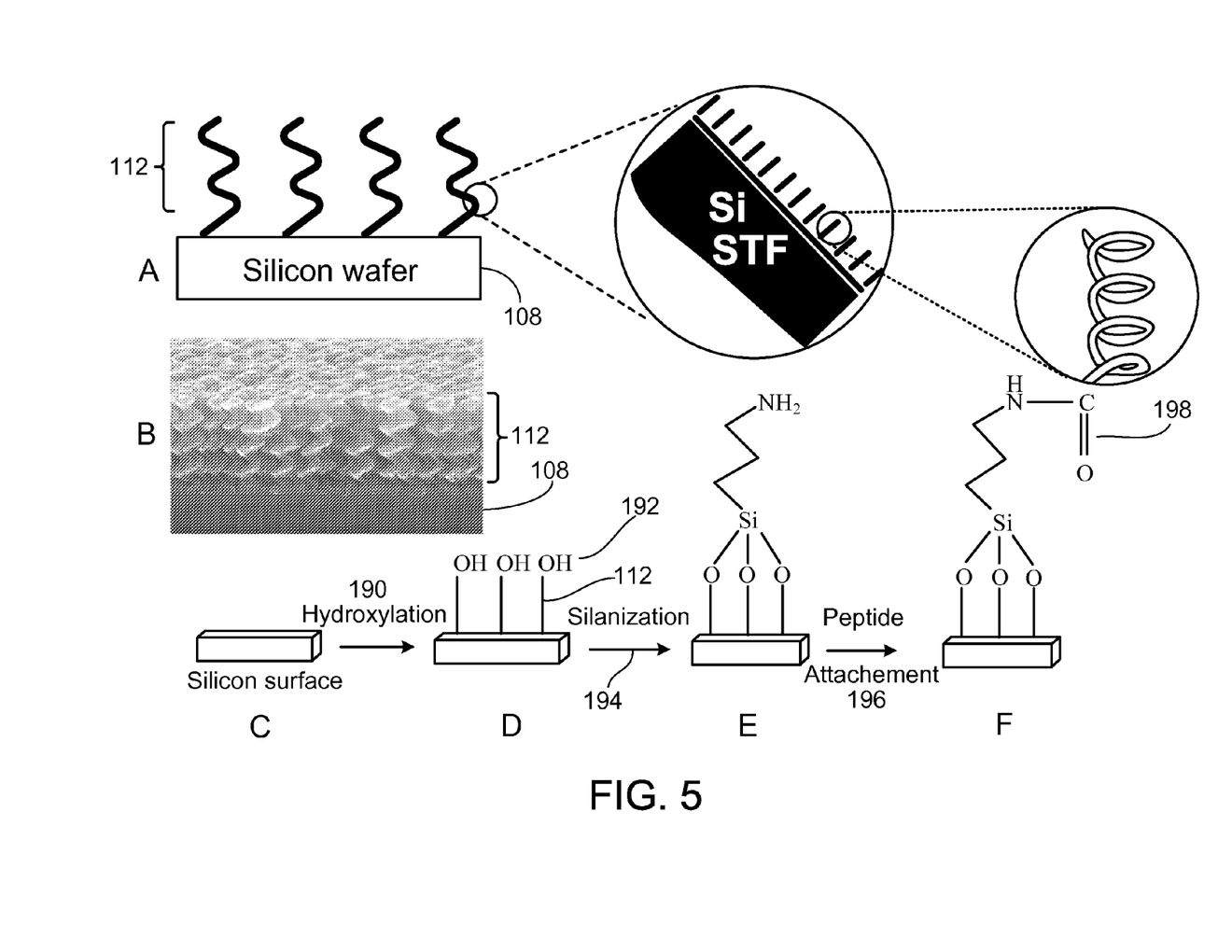
FIG. 5 is a diagram of a process for providing functional attachments to nanostructures.

Referring to FIG. 5, in some implementations, the nanostructures 112 can be treated to have functional attachments that are configured to selectively capture a predetermined type of objects. In step A, chiral nanostructures 112 are formed on a silicon wafer 108 by glancing angle deposition, resulting in a film of chiral nanostructures 112 as shown in step B. In step C, the surface of the mass sensor 102 is treated by hydroxylation 190 such that hydroxyl (OH) groups 192 are attached to the ends of the nanostructures 112. In step D, the mass sensor 102 is functionalized by applying a silanization treatment 194. In step E, functional attachments, such as peptides 198, are attached 196 to the terminals of the nanostructures 112, resulting in the final product in step F. The chemical treatment sequence shown in FIG. 5 can be replaced by other treatment sequences.

Figure 6:
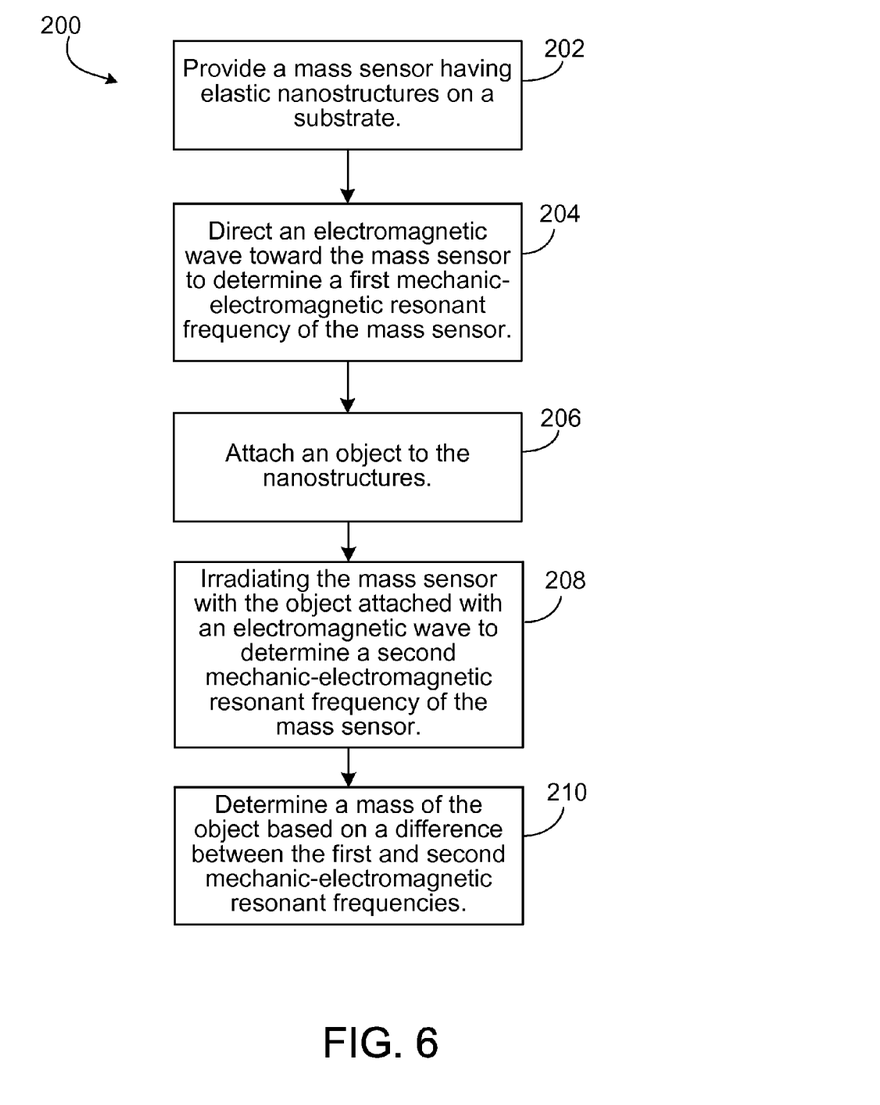
FIG. 6 is a flow diagram of an example process for measuring the mass of an object.

FIG. 6 is a flow diagram of example process 200 for measuring the mass of a small object. In process 200, a mass sensor having nanostructures on a substrate is provided 202. For example, the mass sensor can be the mass sensor 102 of FIG. 1, the nanostructures can be the nanostructures 112, and the substrate can be the substrate 108.

An electromagnetic wave is directed towards the mass sensor to determine a first mechanical-electromagnetic resonant frequency of the mass sensor 204. For example, the ellipsometer 104 of FIG. 1 can be used to measure the first mechanical-electromagnetic resonant frequency of the mass sensor 102.

An object is attached to the nanostructures 206.

Another electromagnetic wave is directed toward the mass sensor with the object attached to determine a second mechanical-electromagnetic resonant frequency of the mass sensor 208.

A mass of the object is determined based on a difference between the first and second mechanical-electromagnetic resonant frequencies 210. For example, the data processing module 106 can determine the mass of the object based on the difference between the first and second mechanical-electromagnetic resonant frequencies. The data processor 116 can compare the difference between the first and second mechanical-electromagnetic resonant frequencies with calibration data 114 to determine the mass of the object.

Although some examples have been discussed above, other implementations and applications are also within the scope of the following claims. For example, the nanostructures 112 can have shapes and sizes that are different from those described above. The substrate 108 can be made from a material that is different from those described above. Electromagnetic wave analyzers other than ellipsometers 104 can be used to measure the eigenresonances of the mass sensor 102. Rather than analyzing electromagnetic waves reflected from the surface of the mass sensor 102, it is also possible to analyze electromagnetic waves transmitted through the sculptured thin film 110 and the substrate 108 to determine changes in the resonant frequency of the mass sensor 102.

The various examples and features described above related to data processing can be implemented in digital electronic circuitry, or in computer hardware, firmware, software, or in combinations of them. The features can be implemented in a computer program product tangibly embodied in an information carrier, e.g., in a machine-readable storage device or in a propagated signal, for execution by a programmable processor; and method steps can be performed by a programmable processor executing a program of instructions to perform functions of the described implementations by operating on input data and generating output.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java), including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

What is claimed is:

1. A method of determining a mass of a particle, the method comprising:
   providing a mass sensor having a plurality of nanostructures on a substrate;
   irradiating the plurality of nanostructures and the substrate with an electromagnetic wave to determine a first mechanical-electromagnetic resonant frequency of the mass sensor such that a resonance occurs when the nanostructures and the substrate are irradiated by an electromagnetic wave having a frequency substantially equal to the first mechanical-electromagnetic resonant frequency;
   attaching a particle to the nanostructures;
   irradiating the substrate and the plurality of nanostructures to which the particle is attached with an electromagnetic wave to determine a second mechanical-electromagnetic resonant frequency of the mass sensor; and
   determining a mass of the particle based on a difference between the first and second mechanical-electromagnetic resonant frequencies.

2. The method of claim 1 in which providing a plurality of nanostructures on a substrate comprises providing a plurality of nanocoil structures on a substrate.

3. The method of claim 1 in which providing a plurality of nanostructures on a substrate comprises providing a plurality of chiral nanostructures on a substrate.

4. The method of claim 1 in which providing a plurality of nanostructures on a substrate comprises providing a plurality of metal nanostructures on a semiconductor substrate.

5. The method of claim 1 in which irradiating the plurality of nanostructures with an electromagnetic wave comprises irradiating the plurality of nanostructures with an electromagnetic wave having a frequency that matches the mechanical-electromagnetic resonant frequency of the nanostructures.

6. The method of claim 5 in which providing a plurality of nanostructures comprises providing a plurality of nanostructures having a mechanical eigenresonance that measurably influence an electromagnetic eigenresonance of the mass sensor, the influence of the mechanical eigenresonance on the electromagnetic eigenresonance being measurable based on measurements of properties of the electromagnetic wave that is transmitted through or reflected from the mass sensor.

7. The method of claim 1 in which determining a mass comprises comparing the difference between the first and second mechanical-electromagnetic resonant frequencies with information representing a mapping between changes in mechanical-electromagnetic resonant frequencies and mass.

8. The method of claim 1, comprising detecting electromagnetic waves that are reflected from the nano structures, and determining the first and second mechanical-electromagnetic resonant frequencies based on the detected electromagnetic waves.

9. The method of claim 1, comprising detecting electromagnetic waves that are transmitted from the nano structures, and determining the first and second mechanical-electromagnetic resonant frequencies based on the detected electromagnetic waves.

10. The method of claim 1 in which attaching a particle comprises selectively capturing a particle that belongs to a type of particles that match a shape of the nanostructures.

11. An apparatus comprising:
    a mass sensor comprising:
        a substrate; and
        a plurality of nanostructures attached to the substrate, the nanostructures having a mechanical resonant frequency that varies depending on a mass of an object coupled to the nanostructures, the nanostructures and the substrate having a mechanical-electromagnetic resonant frequency such that a resonance occurs when the nanostructures and the substrate are irradiated by an electromagnetic wave having a frequency substantially equal to the mechanical-electromagnetic resonant frequency;

wherein the plurality of nanostructures and the substrate are configured such that changes in the mechanical-electromagnetic resonant frequencies correspond to the mass of the object according to a predetermined mapping between changes in mechanical-electromagnetic resonant frequencies and mass.

12. The apparatus of claim 11 in which the nanostructures comprise nanocoil structures.

13. The apparatus of claim 11 in which at least 10% of the nanostructures each comprises a nanowire having a diameter less than 500 nm.

14. The apparatus of claim 11 in which the nanostructures comprise chiral nanostructures.

15. The apparatus of claim 11 in which the nanostructures and the substrate have dimensions and materials configured such that the mechanical-electromagnetic resonant frequency of the mass sensor is in a range from 0.1 to 20.5 terahertz, the mechanical-electromagnetic resonant frequency being adjustable depending on a bias voltage applied to the substrate.

16. The apparatus of claim 11 in which the nanostructures comprise metal, and the substrate comprises a semiconductor.

17. The apparatus of claim 11 in which the plurality of nanostructures comprise a first group of nanostructures and a second group of nanostructures, the first group of nanostructures having a first lateral spacing period, the second group of nanostructures having a second lateral spacing period that is different from the first lateral spacing period.

18. The apparatus of claim 11, comprising a first electrode and a second electrode to receive a bias voltage, the first and second electrodes being coupled to the substrate to provide the bias voltage to the substrate.

19. The apparatus of claim 11 in which the nanostructures have shapes configured to selectively capture a predetermined type of objects.

20. The apparatus of claim 11 in which the nanostructures are treated to have functional attachments that are configured to selectively capture a predetermined type of objects.

21. The apparatus of claim 20 in which the functional attachments comprise peptides.

22. A system for measuring a mass of an object, comprising:
    a mass sensor comprising:
        a substrate; and
        a plurality of nanostructures attached to the substrate;
    an analyzer to determine a mechanical-electromagnetic resonant frequency of the mass sensor; and
    a data processor to determine a mass of an object attached to the nano structures based on a difference between a first mechanical-electromagnetic resonant frequency of the mass sensor measured before the object is attached to the nano structures and a second mechanical-electromagnetic resonant frequency of the mass sensor measured after the object is attached to the nano structures, the nano structures and the substrate having a mechanical-electromagnetic resonant frequency such that a resonance occurs when the nano structures and the substrate are irradiated by an electromagnetic wave having a frequency substantially equal to the mechanical-electromagnetic resonant frequency.

23. The system of claim 22 in which the nanostructures comprise at least one of nanocoil structures or chiral nanostructures.

24. The system of claim 22 in which the nanostructures comprise metal, and the substrate comprises a semiconductor.

25. The system of claim 22 in which the analyzer comprises an ellipsometer.

26. The system of claim 22, comprising a voltage source to provide a bias voltage to the substrate, and a controller to control the voltage source to adjust the bias voltage to change the mechanical-electromagnetic resonant frequency of the mass sensor.

27. The system of claim 26 in which the nanostructures and the substrate have dimensions and materials configured such that a mechanical eigenresonance of the nanostructures couples with an electromagnetic eigenresonance of the mass sensor, and the coupled mechanical-electromagnetic resonant frequency matches a frequency range of the analyzer, which uses electromagnetic waves to determine the mechanical-electromagnetic eigenresonance of the mass sensor.

28. The system of claim 22, comprising a storage to store information representing a mapping between changes in the mechanical-electromagnetic resonant frequency and mass.

29. The system of claim 22 in which the nano structures have shapes configured to selectively capture a predetermined type of objects.

30. The system of claim 22 in which the nano structures are treated to have functional attachments that are configured to selectively capture a predetermined type of objects.

31. The system of claim 22 in which the plurality of nanostructures comprise a first group of nanostructures and a second group of nanostructures, the first group of nanostructures having a first lateral spacing period, the second group of nanostructures having a second lateral spacing period that is different from the first lateral spacing period.

32. The system of claim 31 in which the mass of the object is determined based on a first difference in mechanical-electromagnetic resonant frequencies in a first region of the mass sensor having the first group of nanostructures and a second difference in mechanical-electromagnetic resonant frequencies in a second region of the mass sensor having the second group of nanostructures.

33. A method of determining a mass of a particle, the method comprising:
    providing a mass sensor having a plurality of nanostructures on a substrate;
    irradiating the plurality of nanostructures and the substrate with an electromagnetic wave to determine a first mechanical-electromagnetic resonant frequency of the mass sensor;
    attaching a particle to the nanostructures;
    irradiating the substrate and the plurality of nanostructures to which the particle is attached with an electromagnetic wave to determine a second mechanical-electromagnetic resonant frequency of the mass sensor; and
    determining a mass of the particle based on a difference between the first and second mechanical-electromagnetic resonant frequencies;
    wherein the nanostructures and the substrate have dimensions and materials configured such that the mechanical-electromagnetic resonant frequency of the mass sensor is in a range from 0.1 to 20.5 terahertz, the mechanical-electromagnetic resonant frequency being adjustable depending on a bias voltage applied to the substrate.

34. A method of determining a mass of a particle, the method comprising:
- providing a mass sensor having a plurality of nanostructures on a substrate;
- irradiating the plurality of nanostructures and the substrate with an electromagnetic wave to determine a first mechanical-electromagnetic resonant frequency of the mass sensor;
- attaching a particle to the nanostructures;
- irradiating the substrate and the plurality of nanostructures to which the particle is attached with an electromagnetic wave to determine a second mechanical-electromagnetic resonant frequency of the mass sensor; and
- determining a mass of the particle based on a difference between the first and second mechanical-electromagnetic resonant frequencies;
- wherein the plurality of nanostructures comprise a first group of nanostructures and a second group of nanostructures, the first group of nanostructures having a first lateral spacing period, the second group of nanostructures having a second lateral spacing period that is different from the first lateral spacing period.

35. A method of determining a mass of a particle, the method comprising:
- providing a mass sensor having a plurality of nanostructures on a substrate;
- irradiating the plurality of nanostructures and the substrate with an electromagnetic wave to determine a first mechanical-electromagnetic resonant frequency of the mass sensor;
- attaching a particle to the nanostructures;
- irradiating the substrate and the plurality of nanostructures to which the particle is attached with an electromagnetic wave to determine a second mechanical-electromagnetic resonant frequency of the mass sensor; and
- determining a mass of the particle based on a difference between the first and second mechanical-electromagnetic resonant frequencies;
- wherein the nanostructures are treated to have functional attachments that are configured to selectively capture a predetermined type of objects.

36. A system for measuring a mass of an object, comprising:
- a mass sensor comprising:
  - a substrate; and
  - a plurality of nanostructures attached to the substrate;
- an analyzer to determine a mechanical-electromagnetic resonant frequency of the mass sensor; and
- a data processor to determine a mass of an object attached to the nano structures based on a difference between a first mechanical-electromagnetic resonant frequency of the mass sensor measured before the object is attached to the nano structures and a second mechanical-electromagnetic resonant frequency of the mass sensor measured after the object is attached to the nano structures;
- wherein the nanostructures and the substrate have dimensions and materials configured such that the mechanical-electromagnetic resonant frequency of the mass sensor is in a range from 0.1 to 20.5 terahertz, the mechanical-electromagnetic resonant frequency being adjustable depending on a bias voltage applied to the substrate.

37. A system for measuring a mass of an object, comprising:
- a mass sensor comprising:
  - a substrate; and
  - a plurality of nanostructures attached to the substrate;
- an analyzer to determine a mechanical-electromagnetic resonant frequency of the mass sensor; and
- a data processor to determine a mass of an object attached to the nano structures based on a difference between a first mechanical-electromagnetic resonant frequency of the mass sensor measured before the object is attached to the nano structures and a second mechanical-electromagnetic resonant frequency of the mass sensor measured after the object is attached to the nano structures;
- wherein the plurality of nanostructures comprise a first group of nanostructures and a second group of nanostructures, the first group of nanostructures having a first lateral spacing period, the second group of nanostructures having a second lateral spacing period that is different from the first lateral spacing period.

38. A system for measuring a mass of an object, comprising:
- a mass sensor comprising:
  - a substrate; and
  - a plurality of nanostructures attached to the substrate;
- an analyzer to determine a mechanical-electromagnetic resonant frequency of the mass sensor; and
- a data processor to determine a mass of an object attached to the nano structures based on a difference between a first mechanical-electromagnetic resonant frequency of the mass sensor measured before the object is attached to the nano structures and a second mechanical-electromagnetic resonant frequency of the mass sensor measured after the object is attached to the nano structures;
- wherein the nanostructures are treated to have functional attachments that are configured to selectively capture a predetermined type of objects.

* * * * *